(12) United States Patent
Herrera et al.

(10) Patent No.: US 11,376,011 B2
(45) Date of Patent: Jul. 5, 2022

(54) CATHETER BALLOON FOR REDUCING TOTAL CARDIAC BURDEN

(71) Applicants: José E. Herrera, Porlamar (VE); José A. Herrera, Barcelona (ES)

(72) Inventors: José E. Herrera, Porlamar (VE); José A. Herrera, Barcelona (ES)

(*) Notice: Subject to any disclaimer, the term of this patent is extended or adjusted under 35 U.S.C. 154(b) by 170 days.

(21) Appl. No.: 16/592,159

(22) Filed: Oct. 3, 2019

(65) Prior Publication Data

US 2021/0100559 A1    Apr. 8, 2021

(51) Int. Cl.
 *A61B 17/12* (2006.01)
 *A61B 17/00* (2006.01)
 *A61M 25/10* (2013.01)

(52) U.S. Cl.
 CPC .... *A61B 17/12136* (2013.01); *A61B 17/1204* (2013.01); *A61B 17/12036* (2013.01); *A61B 17/12109* (2013.01); *A61B 2017/00539* (2013.01); *A61B 2017/00725* (2013.01); *A61M 2025/1086* (2013.01)

(58) Field of Classification Search
 CPC ........ A61B 17/12136; A61B 17/12036; A61B 17/1204; A61B 17/12109; A61B 2017/00539; A61B 2017/00725; A61B 2017/00699; A61M 2025/1086; A61M 25/1002; A61M 2210/125; A61M 2025/1095
 USPC ........................................ 604/103.08, 101.01
 See application file for complete search history.

(56) References Cited

U.S. PATENT DOCUMENTS

| | | | | |
|---|---|---|---|---|
| 5,135,474 A | * | 8/1992 | Swan | A61M 25/1011 604/101.05 |
| 5,250,070 A | * | 10/1993 | Parodi | A61M 25/104 604/103.08 |
| 2013/0102926 A1 | * | 4/2013 | Eliason | A61B 5/1076 600/585 |

* cited by examiner

*Primary Examiner* — Julian W Woo
(74) *Attorney, Agent, or Firm* — Ference & Associates LLC

(57) ABSTRACT

An embodiment provides a method for normalizing cardiac venous return, including: inserting percutaneously a calibrated balloon catheter through a femoral vein; advancing the calibrated balloon catheter to the inferior vena cava; and placing a balloon portion of the calibrated balloon catheter at a location before the drainage point of the hepatic vein.

10 Claims, 8 Drawing Sheets

LEGEND

1.- Balloon Wall.
2.- Balloon Shaft.
3.- Windows Shaft.
4.- Balloon Groove
5.- Inferior Vana Cava Wall
6.- Inferior Vena Cava blood
7.- SubTotal Occlusion
8.- External Balloon Diameter.
9.- Balloon Distal End

CATHETER BALLOON FOR REDUCING TOTAL CARDIAC BURDEN

FIELD

This application relates generally to cardiac catheters, and, more particularly, to a balloon catheter for reducing venous return.

BACKGROUND

Acute heart failure (AHF) may also be known as acute decompensated heart failure or cardiac failure. AHF may manifest as signs and symptoms worsen over time due to the inability of the heart to pump blood at a rate for the needs of the body at normal filling pressure. AHF may develop over the course of days to weeks. AHF may be a result in disturbance of systolic or diastolic function of the heart or abnormal venous or arterial vasoconstriction. Often, the cardiac system experiences a volume overload. Common symptoms may include dyspnea, fatigue, cough, abdominal discomfort, leg pain, sleep disturbances, edema of the lower extremities, or the like. Patients may present with all or just some of these symptoms. In the United States, heart failure is the leading cause of hospitalization in patients over 65 years of age. Patients may be prescribed medication to reduce fluid volume, increase vascular flow, increase cardiac output, or the like. However, the cost, side effects, and patient compliance remain a barrier to effective treatment.

BRIEF SUMMARY

In summary, one embodiment provides a method for normalizing cardiac venous return, comprising: inserting percutaneously a calibrated balloon catheter through a femoral vein; advancing the calibrated balloon catheter to the inferior vena cava; and placing a balloon portion of the calibrated balloon catheter at a location before the drainage point of the hepatic vein.

Another embodiment provides a device for normalizing cardiac venous return, comprising: a calibrated balloon catheter, comprising a balloon portion and a shaft portion; the calibrated balloon catheter being configured to: insert percutaneously the calibrated balloon catheter through a femoral vein; advance the calibrated balloon catheter to the inferior vena cava; and place the balloon portion of the calibrated balloon catheter at a location before the drainage point of the hepatic vein.

A further embodiment provides a method for normalizing cardiac venous return, comprising: inserting percutaneously a calibrated balloon catheter through a femoral vein wherein the calibrated balloon catheter is calibrated to a degree of collapse during inspiration of a patient inferior vena cava; advancing the calibrated balloon catheter to the inferior vena cava, wherein the calibrated balloon catheter intermittently occludes the inferior vena cava during patient inspiration; and placing a balloon portion of the calibrated balloon catheter at a location before the drainage point of the hepatic vein, wherein the balloon catheter free-floats in the inferior vena cava without an active fixation point between the balloon catheter and an inner lumen of the inferior vena cava.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
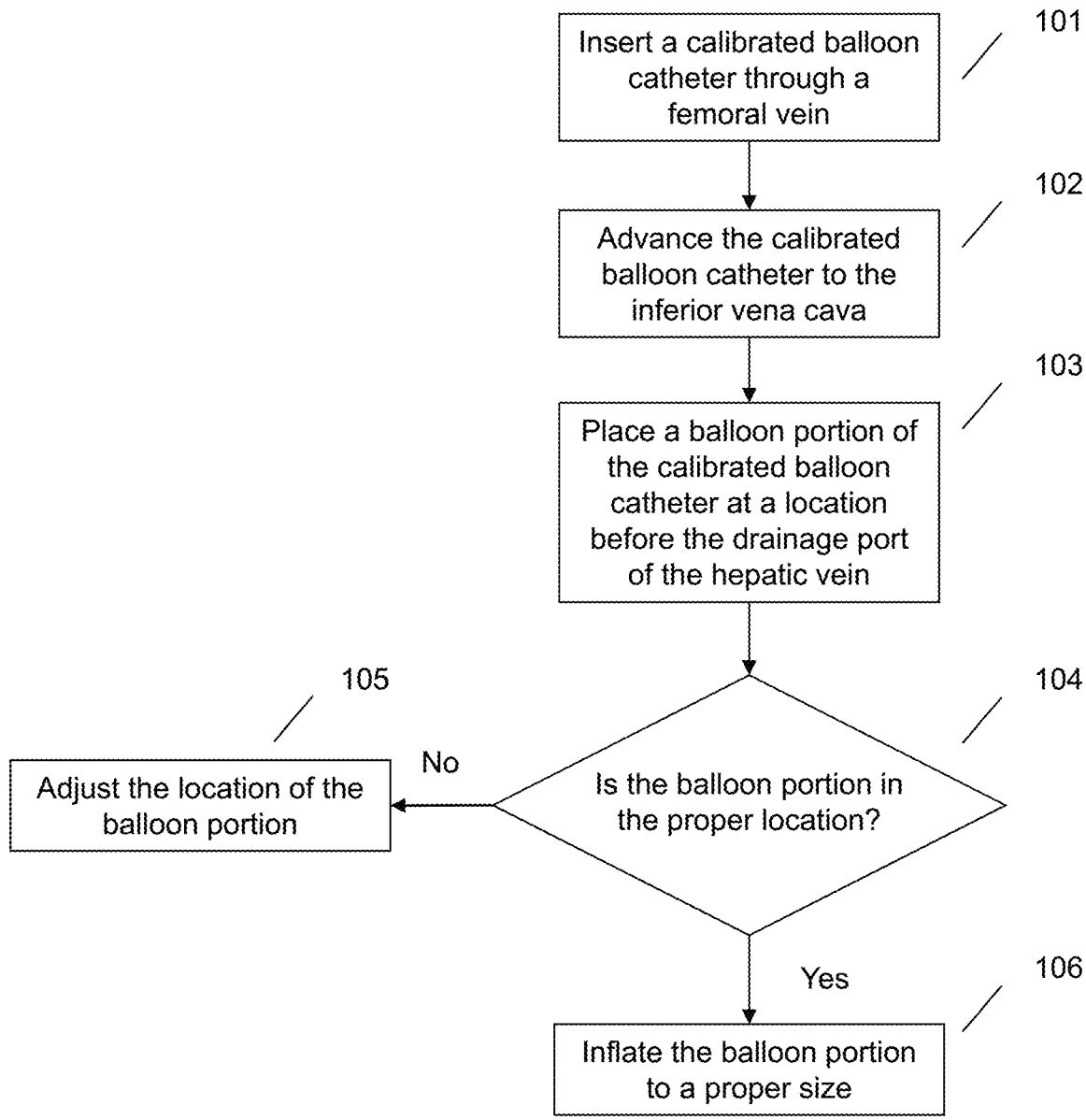
FIG. 1 illustrates a block diagram of an embodiment of a balloon catheter.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Acute heart failure may be a result of the increase of the venous return which causes volume overload and severe pulmonary congestion. The decrease of venous return (normalization) may be crucial in the improvements of the symptoms of pulmonary congestion and heart failure. In early attempts to solve the problem, bloodletting and tourniquet in the lower extremities were used as a means to normalize venous return, to improve the pulmonary congestion. In later years, the use of mercurial diuretics, stronger ASA diuretics, furosemide, and bumetanide helped to rapidly decrease the venous return, with improvements of the heart failure symptoms. However, there were possible deleterious effects on the renal function, such as hydro-electrolytic disorders and renal damages. The persistence of the problem of the increased venous return led to the use of nitride and nitrates, which produce a venous dilatation, causing a reduction on the venous return, improving the symptoms for a short period of time. However, the inherent intolerance in this type of medication may cause the loss of the effect in a few months, with the additional inconvenience of associated headaches as a side effect. The introduction of receptor blockers of aldosterone (spironolactona), hydro saline retention was minimized, as well as venous return. However, the receptor blockers produced serious side effects.

Later, new pharmacological alternatives were introduced such as drugs that block the formation of angiotensin, which produced the decrease of venous return, improving the quality of life of a patient with heart failure. Subsequently, the use of beta blockers to produce benefits in patients with heart failure, being a treatment choice for a high number of patients with heart failure. The advent of receptor blockers (V1-V2) of the neuro-hormonal arginine-vasopressin axis, a reducer of corporal water, decrease of venous return and improvement of pulmonary congestion may be achieved for a very short period of time and at an extremely high price. The use of stem cells for the treatment of heart failure was assessed at the Annual Meeting of The American Heart Association 2007. This technique caused little improvement in the ejection fraction of the left ventricle, and better results are obtained only when the venous return is diminished through diuretic administration.

What is needed is a method and device for treating acute heart failure (AHC). If a patient present in an emergency department, a relatively fast and reliable way to reduce hypervolemia may improve patient outcome. The method and device may reduce venous return for a temporary period of time until normal levels of cardiac function are achieved.

Accordingly, an embodiment provides a method and device for the regulating hypervolemia. In particular, the method and device may reduce venous return. The method and device may use an inflatable balloon catheter. The balloon catheter may be calibrated. The calibration may be such that the inferior vena cava (IVC) is occluded during the inspiratory phase of patient breathing. Blood flow may be restored upon expiratory phase of patient breathing. The balloon catheter may be inserted through the left or right femoral vein. The balloon catheter may be advance into the inferior vena cava to a point before the entry of the hepatic drain. The balloon catheter may be free floating. In an embodiment, the balloon catheter may have a shaft extending from the point of insertion to the balloon catheter. The balloon catheter may be free floating in the venous system. The balloon catheter may have no active fixation point at the distal balloon catheter end. In an embodiment, there may be a fixation at the proximal or insertion end.

The illustrated example embodiments will be best understood by reference to the figures. The following description is intended only by way of example, and simply illustrates certain example embodiments.

Figure 2:
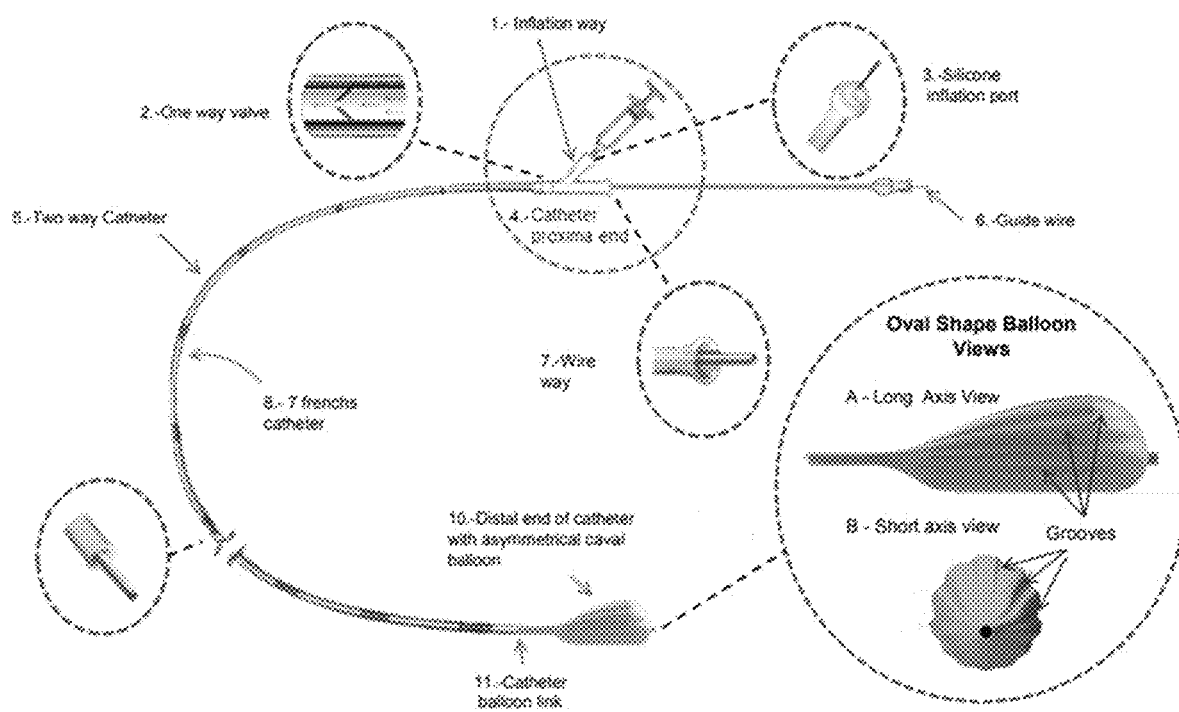
FIG. 2 illustrates an example embodiment of a balloon catheter.

Referring to FIG. 1, an embodiment of a calibrated balloon catheter is described. The calibrated balloon catheter may be used for the treatment of AHF. The calibrated balloon catheter may be used to decrease or to normalize venous blood return. The calibrated balloon catheter may have a proximal end and a distal end. The distal end may have a balloon portion. The balloon portion may be free floating. In other words, there may be no fixation means on the distal end of the calibrated balloon catheter. The proximal end may have a fixation mechanism. The proximal end and the distal end may be connected by a shaft. An example embodiment of placement of the calibrated balloon catheter is illustrated by FIG. 2 and within the corresponding specification. Example embodiments of the calibrated balloon catheter are illustrated in FIGS. 3 through 8, and corresponding portions of the specification.

At 101, in an embodiment, the calibrated balloon catheter may be inserted through either the left or right femoral vein. In an embodiment, the distal end of the calibrated balloon catheter with a balloon portion may be inserted first, then the shaft, with the proximal end of the calibrated balloon catheter near the insertion site. In an embodiment, the shaft may allow for a rigid structure for the insertion and placement of the calibrated balloon catheter. Further embodiments regarding the shaft are described herein.

At 102, in an embodiment, the calibrated balloon catheter may be advanced to a patient inferior vena cava (IVC). The advancement of the calibrated balloon catheter may be performed using real-time imaging techniques, such as 2D echocardiography. The IVC may be imaged in a sub-coastal position, long axis view, and/or the diameter measured during patient inspiration (breath in). The imaging and measurements may be used for placement of the balloon portion or for the proper sizing for inflation of the balloon.

At 103, in an embodiment, the calibrated balloon catheter may be placed such that the balloon portion of the calibrated balloon catheter is at a location before the drainage port of the hepatic vein. An embodiment of the balloon portion placement may be illustrated in FIG. 3 and the corresponding specification. At 104, the method and device may confirm that the balloon portion is in a proper position. In an embodiment, the proper position would be such that the balloon portion of the calibrated balloon catheter is located before the hepatic drainage in the IVC. At 105, if the location of the balloon portion is not proper, then the position of the balloon portion may be adjusted. Adjustment may be performed using real-time imaging techniques.

At 106, in an embodiment, the method and device may inflate the balloon portion to a proper size. In an embodiment, the balloon portion may be inflated using saline. The saline may be injected through a port on the proximal end. The balloon portion may be inflated to a size such that venous occlusion occurs during inspiration (breathing in), and partial occlusion occurs during expiration (breathing out). In an embodiment, the calibrated balloon catheter may reduce (normalize) venous return, reducing total cardiac burden, or the like.

Referring to FIG. 2, in an embodiment, the device may be a balloon catheter. The balloon catheter may be inserted through the left or right femoral vein. The balloon catheter may be advanced to the IVC of a patient. The balloon catheter may be advanced to a point in the IVC such that the balloon on the distal end is in a position before the hepatic drainage. Further detail of a balloon catheter embodiment and example placement in a patient venous system may be illustrated in FIG. 8.

The balloon catheter may have a distal end and a proximal end. The proximal end may be at the point of insertion. The proximal end may have a fixation point. The fixation point may allow the fixation of the proximal end or near the proximal end to subcutaneous cellular tissue, or the like. The proximal end may be bifurcated. The proximal end may have at least one port. The port may be a silicone inflation port. The ports may allow for the addition or removal of material to inflate or deflate the balloon catheter. The material for filling the balloon may be saline, or the like. The proximal end and the distal end may be connected by a shaft. The shaft may be a two-way catheter, 7 French catheter, or the like. In an embodiment, the lumen of the catheter may have a one-way valve. In an embodiment, a guide wire may pass though the proximal end along the length of the catheter.

The balloon catheter may be calibrated. In other words, the balloon size or inflation size may be selected to occlude venous blood flow during the inspiratory phase of breathing and allow venous flow during expiration. A balloon may be on the distal end. Calibration may include sizing the balloon catheter. A balloon may be sized or selected prior to insertion depending on anatomical measurement of the IVC diameter during inspiration of a patient. The anatomical measurements may include an IVC luminal diameter. The balloon may be inflated, sized, calibrated, or the like once the balloon catheter and distal balloon are placed in the IVC. For example, imaging performed pre-procedure or in real-time may allow a healthcare professional to properly inflate the balloon in the IVC to block venous flow during inspiration and allow venous flow during expiration phases of breathing.

In an embodiment, the balloon catheter may include a one-way catheter for balloon inflation. The balloon may be made of polyurethane. The balloon may have a plurality of slots or groves upon an outer surface. The balloon may have 8 slots or groves upon an outside surface. The one or more slots or grooves may be 2 millimeters (mm) wide by 1 mm deep. The number of grooves and dimensions are illustrative, and may be altered for proper balloon fitting within the IVC. In an embodiment, the balloon may have a smaller anteroposterior diameter. In other words, the end of the balloon facing the blood flow may have a smaller diameter as compared to the diameter of the trailing edge end of the balloon facing downstream blood flow. The shape of the balloon may offer less resistance to blood flow. The shape may allow the balloon to float freely, attached to the shaft of the catheter. In an embodiment, the balloon is not actively fixated to the walls or inner lumen of the IVC.

Figure 3:
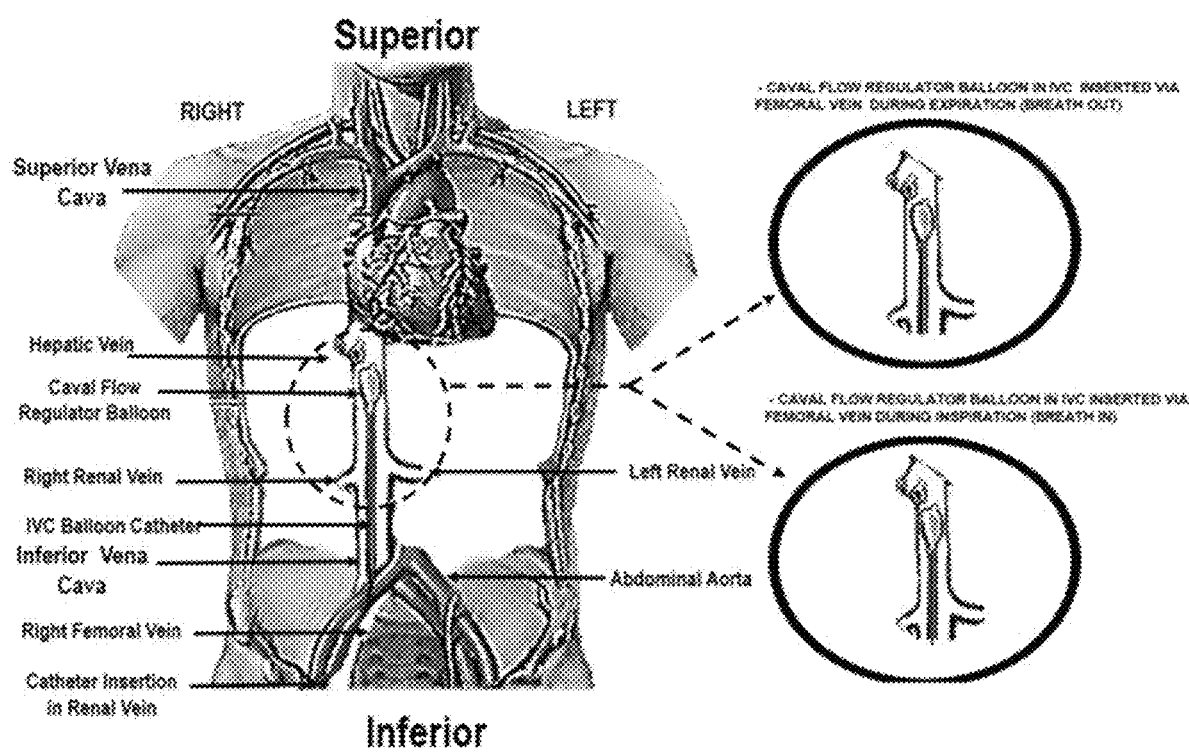
FIG. 3 illustrates an example embodiment of a balloon catheter placement in a patient.

Referring to FIG. 3, in an embodiment the device may be implanted into a patient. For example, the balloon catheter may be inserted through the left or right femoral vein. The balloon catheter may be advanced up through the IVC to a point at which the balloon is positioned before the hepatic drain or hepatic vein. The balloon of the balloon catheter may be free floating without a fixation point in the IVC. A fixation point may be present at the proximal end near the point of insertion. The FIG. 3 insets illustrate the balloon catheter during an expiration phase of respiration (top inset), and during an inspiration phase of respiration (bottom inset).

Figure 4:
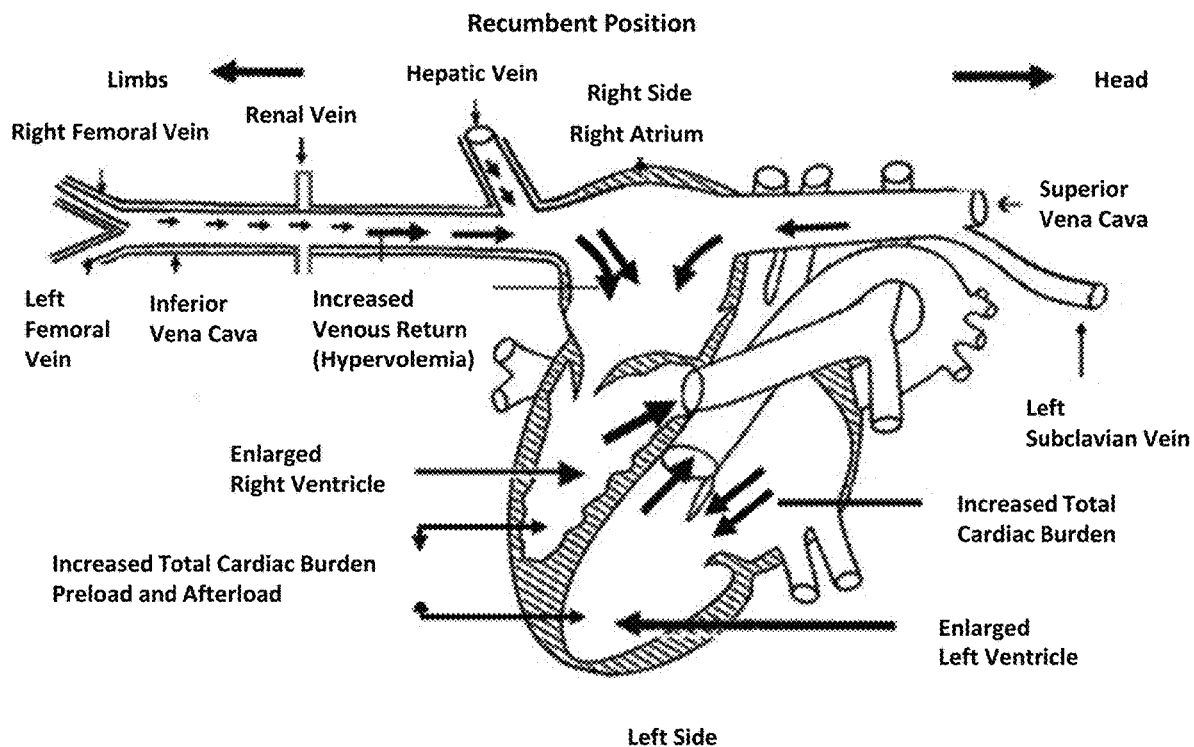
FIG. 4 illustrates an example cardiac function of a patient with heart failure.

Referring to FIG. 4, an illustration of a cardiovascular system of a patient presenting with acute heart failure is illustrated. For example, the patient may have increased venous return or hypervolemia. The increased venous return may lead to increased total cardiac burden. The increased total cardiac burden may be defined as a preload and afterload. For example, the right, left, or both ventricles may be enlarged. There may be an increased volume of at least one ventricle during diastole and/or systole. The increase in size may result in an increased diameter of the left, right, or both ventricles, which may lead to an increased afterload and total cardiac burden.

Figure 5:
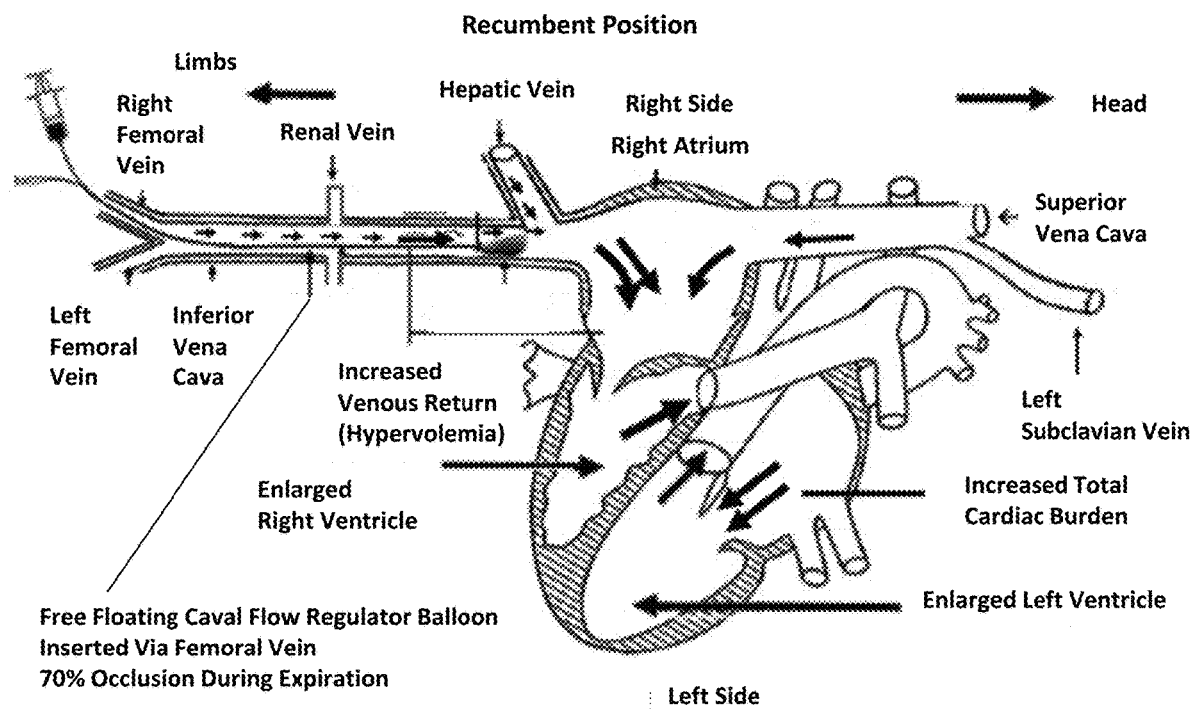
FIG. 5 illustrates an example embodiment of cardiac function after a balloon catheter placement during an expiratory phase of breathing.

Referring to FIG. 5, an example of a cardiovascular system of a patient presenting with acute heart failure is illustrated with the balloon catheter inserted. For example, the heart of a patient in recumbent position with heart failure is illustrated. The left and right ventricles may be dilated. The dilation may be due to intracardiac flow by an increased cardiac venous return or hypervolemia. This may produce an increased total cardiac burden. In an embodiment, a balloon catheter may be inserted through the right femoral vein. The balloon catheter may be advanced to the IVC such that the balloon is placed before the hepatic vein drainage. For example, the balloon may inflated such that 70% of a cross section of the inner lumen of the IVC is occluded during expiration of the patient. For example, if the patient demonstrates an inspiratory collapse of 30% of the cross section of the luminal diameter, then the balloon may occlude the IVC during inspiration. Thus, as a patient expires (breaths out) the flow through the IVC is partially restored.

Figure 6:
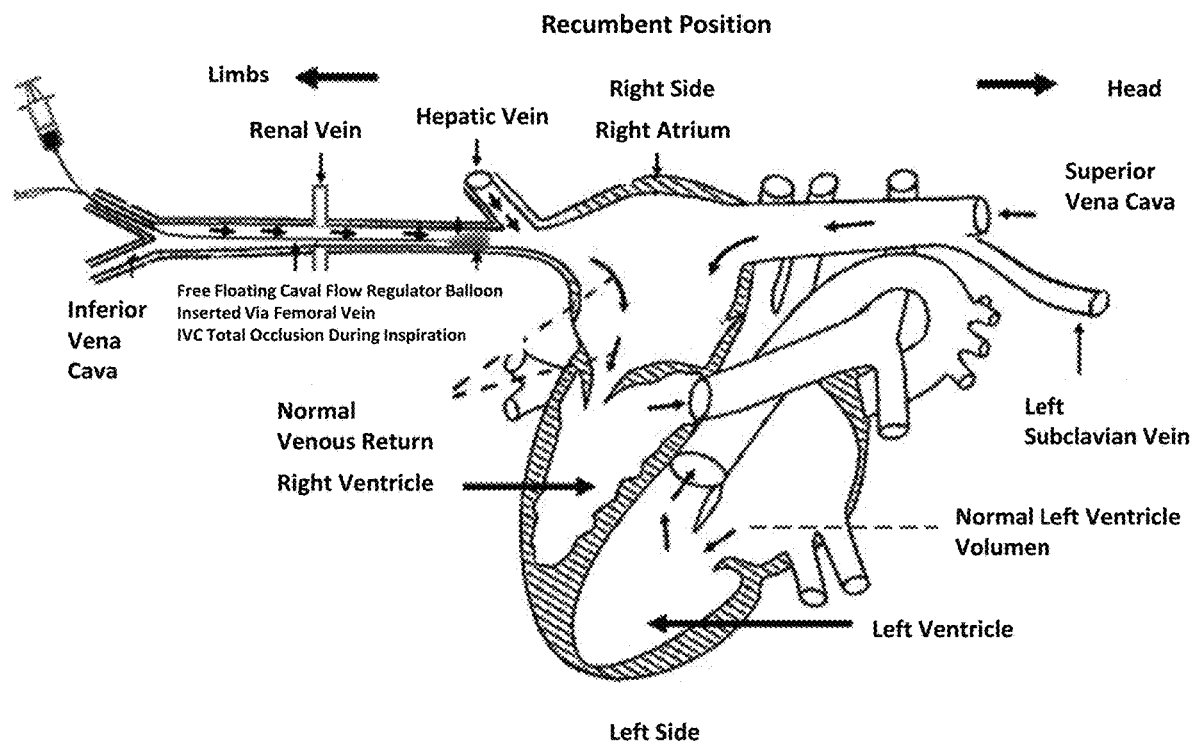
FIG. 6 illustrates an example embodiment of cardiac function after a balloon catheter placement during an inspiratory phase of breathing.

Referring to FIG. 6, an example of a cardiovascular system of a patient presenting with acute heart failure is illustrated with the balloon catheter inserted. For example, the heart of a patient in with heart failure is illustrated during inspiration (breathing in). For example, dilated right and left cavities and evidence of intracardiac flow increased by a cardiac venous return increased or hypervolemia may produce an increased total cardiac burden. In an embodiment, a balloon catheter may be inserted through the right femoral, advanced to the IVC before the drainage of the hepatic vein, and inflated up to 70% of the anteroposterior diameter of the IVC in a patient with an inspiratory collapse of 30%. In an embodiment, when the IVC inspiratory collapse occurs, the anteroposterior diameter of the IVC reduces by 30% and a blood flow regulation occurs for the time that inspiration occurs. In an embodiment, an instantaneous and intermittent reduction of the flow from the IVC to the right atrium during inspiration. When the inspiration ceases, a subtotal occlusion of 70% of the anteroposterior diameter of the IVC occurs, thus allowing the blood flow from the IVC to the right atrium. This may be repeated until achieving a significant reduction of the preload and/or reducing the total cardiac burden in time.

Figure 7:
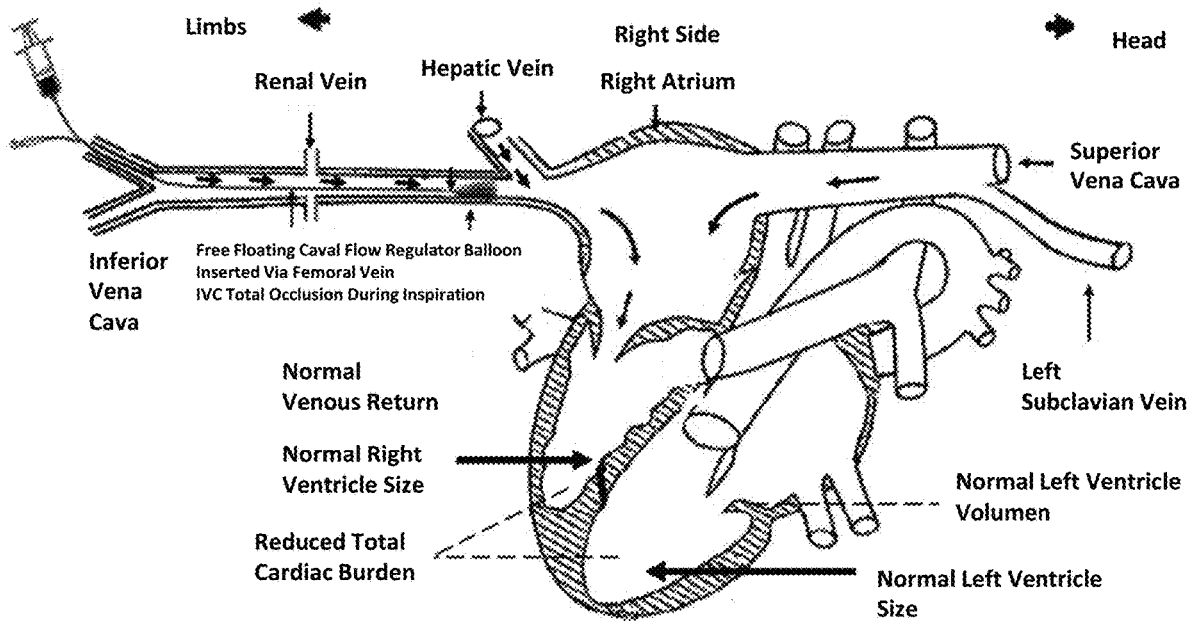
FIG. 7 illustrates an example embodiment of cardiac function after a balloon catheter placement after reduction of total cardiac burden.
Figure 8:
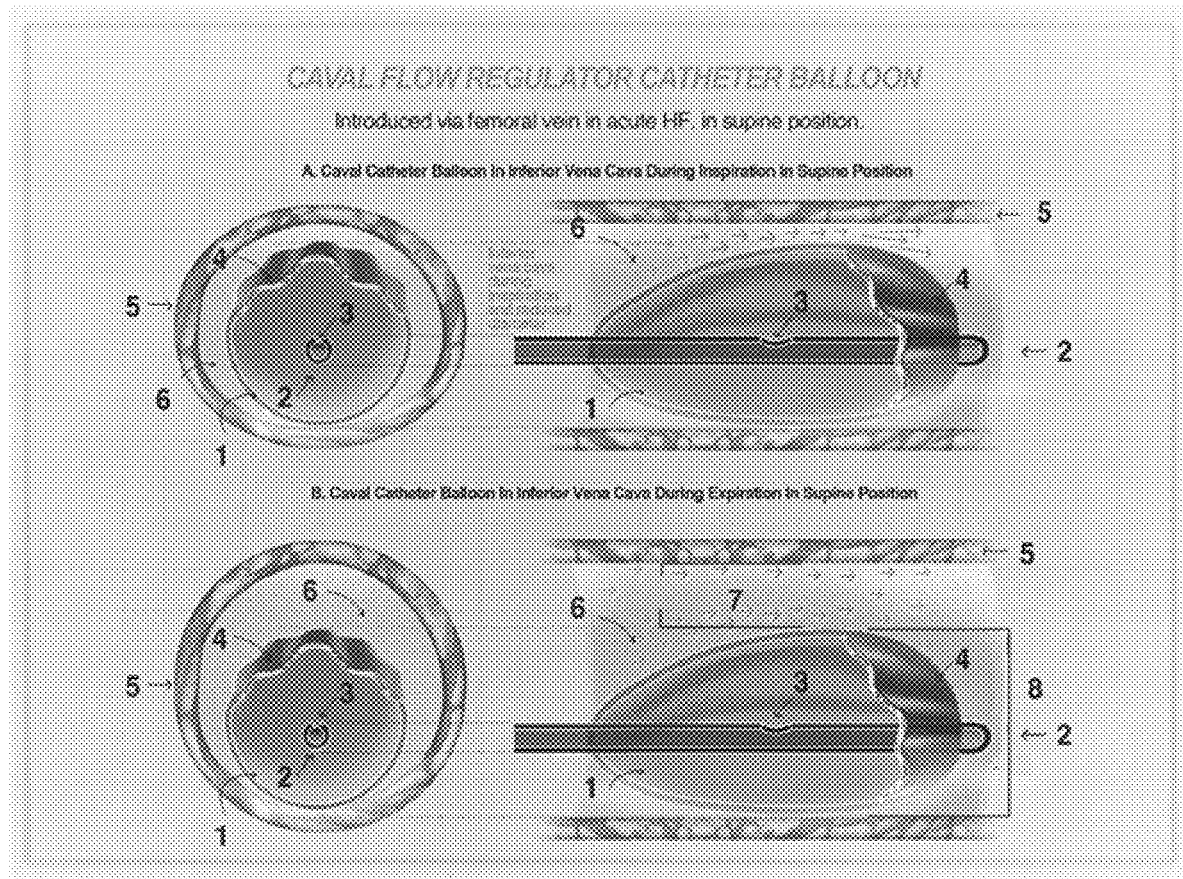
FIG. 8 illustrates an example embodiment of a balloon catheter in a vein.

Referring to FIG. 7, an example of a cardiovascular system of a patient with cardiac chambers of normal size and volume of normal flow with decreased total cardiac burden is illustrated with the balloon catheter inserted. For example, a significant reduction of venous return or preload is illustrated. In an embodiment, the application of this balloon catheter may be used for a period of minutes or several hours during the day or for succeeding days. A time of use of the balloon catheter may be selected to manage acute heart failure. The duration of use of the balloon catheter may be specific to a patient and determined by a medical professional. The method and device may decrease the dose of diuretics to a minimum. The system and method may be used where diuretics are not indicated, such as in pregnancy, or in patients where there is hypersensitivity or tolerance to diuretic medication.

The various embodiments described herein thus represent a technical improvement the treatment of acute heart failure. Using the techniques as described herein, an embodiment may use a method and device to control venous return. The method and device provides a faster, reliable way to reduce venous flow and reduce total cardiac burden. The method and system may be used for a duration specific to the needs of a specific patient. This is in contrast to conventional methods with limitations mentioned above. Such techniques provide a better method to normalize venous return and improve outcomes for patients presenting with acute heart failure. This method may produce normalization of the venous return producing intermittent occlusion of the IVC flow when it is synchronized with the respiratory phases, thus achieving a Percutaneous Transluminal Caval Flow Regulation.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for normalizing cardiac venous return, comprising:
    inserting percutaneously a calibrated balloon catheter through a femoral vein;
    advancing the calibrated balloon catheter to the inferior vena cava; and
    placing a balloon portion of the calibrated balloon catheter at a location before the drainage point of the hepatic vein, wherein the balloon portion of the calibrated balloon catheter comprises a smaller diameter on a proximal end as compared to a distal end.

2. The method of claim 1, wherein the calibrated balloon catheter further comprises a two-way catheter located between the distal end of the calibrated balloon catheter and a point of insertion of the calibrated balloon to a patient body.

3. The method of claim 1, wherein the calibrated balloon catheter is calibrated to a degree of collapse during inspiration state of a patient inferior vena cava.

4. The method of claim 1, wherein the balloon portion of the calibrated balloon catheter intermittently occludes the inferior vena cava during an inspiration phase of patient breathing.

5. The method of claim 1, wherein the balloon portion of the calibrated balloon catheter allows blood flow through the inferior vena cava during an expiration phase of patient breathing.

6. The method of claim 1, wherein the calibrated balloon catheter is filled with saline.

7. The method of claim 1, wherein the balloon portion of the calibrated balloon catheter comprises a plurality of grooves oriented lengthwise on the outer surface.

8. The method of claim 1, wherein the balloon portion of the calibrated balloon catheter free-floats in the inferior vena cava without an active fixation point between the balloon portion of the calibrated balloon catheter and an inner lumen of the inferior vena cava.

9. The method of claim 1, wherein the calibrated balloon catheter remains in place for a time period required to return a total cardiac burden to a normal level.

10. A method for normalizing cardiac venous return, comprising:
    inserting percutaneously a calibrated balloon catheter through a femoral vein wherein the calibrated balloon catheter is calibrated to a degree of collapse during inspiration state of a patient inferior vena cava;
    advancing the calibrated balloon catheter to the inferior vena cava, wherein the calibrated balloon catheter intermittently occludes the inferior vena cava during patient inspiration; and
    placing a balloon portion of the calibrated balloon catheter at a location before the drainage point of the hepatic vein, wherein the balloon catheter free-floats in the inferior vena cava without an active fixation point between the balloon catheter and an inner lumen of the inferior vena cava, wherein the balloon portion of the calibrated balloon catheter comprises a smaller diameter on a proximal end as compared to a distal end.

* * * * *